US009139816B2

(12) United States Patent
Handa et al.

(10) Patent No.: US 9,139,816 B2
(45) Date of Patent: Sep. 22, 2015

(54) VIRAL PARTICLE-LIKE STRUCTURE IN PHYSIOLOGICAL CONDITIONS, AND METHOD OF FORMING IT

(75) Inventors: Hiroshi Handa, Yokohama (JP); Akira Nakanishi, Yokohama (JP); Masaaki Kawano, Yokohama (JP)

(73) Assignee: TOKYO INSTITUTE OF TECHNOLOGY, Meguro-ku, Tokyo (JP)

( * ) Notice: Subject to any disclaimer, the term of this patent is extended or adjusted under 35 U.S.C. 154(b) by 768 days.

(21) Appl. No.: 12/849,437

(22) Filed: Aug. 3, 2010

(65) Prior Publication Data

US 2011/0135718 A1 Jun. 9, 2011

Related U.S. Application Data

(63) Continuation of application No. 11/630,954, filed as application No. PCT/JP2005/012524 on Jun. 30, 2005, now abandoned.

(30) Foreign Application Priority Data

Jul. 1, 2004 (JP) ................................. 2004-195822

(51) Int. Cl.
| | |
|---|---|
| *C12Q 1/70* | (2006.01) |
| *A61K 6/00* | (2006.01) |
| *A61K 39/12* | (2006.01) |
| *C12N 7/00* | (2006.01) |
| *C07K 14/005* | (2006.01) |
| *A61K 39/00* | (2006.01) |

(52) U.S. Cl.
CPC . *C12N 7/00* (2013.01); *A61K 39/12* (2013.01); *C07K 14/005* (2013.01); *A61K 2039/5258* (2013.01); *C12N 2710/22022* (2013.01); *C12N 2710/22023* (2013.01)

(58) Field of Classification Search
None
See application file for complete search history.

(56) References Cited

U.S. PATENT DOCUMENTS

| | | | |
|---|---|---|---|
| 6,046,173 | A | 4/2000 | Forstova et al. |
| 6,420,160 | B1 | 7/2002 | Bloch |
| 6,613,749 | B1 | 9/2003 | Forstova et al. |
| 6,830,929 | B1 | 12/2004 | Sandalon et al. |
| 6,962,777 | B1 | 11/2005 | McCarthy et al. |
| 2001/0021385 | A1 | 9/2001 | Volkin et al. |
| 2003/0096259 | A1 | 5/2003 | McCarthy et al. |
| 2004/0152181 | A1 | 8/2004 | McCarthy et al. |

FOREIGN PATENT DOCUMENTS

| | | |
|---|---|---|
| CA | 2235347 | 5/2007 |
| EP | 1700911 | 9/2006 |
| EP | 1 785 433 | 5/2007 |
| JP | 2000-511773 | 9/2000 |
| JP | 2002-500637 | 1/2002 |
| JP | 2002-360266 | 12/2002 |
| JP | 2010135520 | 9/2010 |
| WO | WO 91/04330 | 4/1991 |
| WO | WO 97/46693 | 1/1997 |
| WO | WO 97/17456 | 5/1997 |
| WO | WO 98/48841 | 11/1998 |
| WO | WO 99/13056 | 3/1999 |
| WO | WO 01/42780 | 6/2001 |
| WO | WO 01/94560 | 12/2001 |
| WO | WO 2004/073738 | 9/2004 |
| WO | WO-2006 004173 | 1/2006 |

OTHER PUBLICATIONS

Gordon-Shaag et al., Cellular Transcription Factor Sp1 Recruits Simian Virus 40 Capsid Proteins to the Viral Packaging Signal, ses, 2002, Journal of Virology, vol. 76, No. 12, pp. 5915-5924.*
Cohen et al., Activation of Rotavirus RNA Polymerase by Calcium Chelation, 1979, Archives of Virology, vol. 60, pp. 177-186.*
Chromy, Laura R. et al., "Chaperone-mediated in vitro assembly of Polyomavirus capsids," PNAS, vol. 100 No. 18, Sep. 2, 2003, pp. 10477-10482.
Ishizu, Ken-Ichiro et al., "Roles of disulfide linkage and calcium ion-mediated Interactions in assembly and disassembly of virus-like particles composed of Simian Virus 40 VP1 capsid protein," Journal of Virology, vol. 75 No. 1, Jan. 2001, American Society for Microbiology, pp. 61-72.
Kimchi-Sarfaty, Chava et al., "High cloning capacity of in vitro packaged SV40 vectors with SV40 virus sequences," Human Gene Therapy, vol. 14, Jan. 20, 2003, pp. 167-177.
Kimchi-Sarfaty, Chava et al., "Brief Report: Efficient delivery of RNA interference effectors via in vitro-packaged SV40 pseudovirons," Human Gene Therapy, vol. 16, Sep. 2005, pp. 1110-1115.
Salunke, Dinakar M., "Self-assembly of purified polyomavirus capsid protein $VP_1$," Cell, vol. 46, 12 Sep. 1986, pp. 895-904.
Kosukegawa, Akinobu et al., "Purification and characterization of virus-like particles and pentamers produced by the expression of SV40 capsid proteins in insect cells," Biochemica et Biophysica Acta, vol. 1290, 1996, pp. 37-45.
Kanesashi, Shin-nosuke et al., "Simian virus 40 VP1 capsid protein forms polymorphic assemblies in vitro," Journal of General Virology, vol. 84, 2003, pp. 1899-1905.
Stokrova, Jitka et al., "Interactions of heterologous DNA with polyomavirus major structural protein, VP1," FEBS Letter, vol. 445, 1999, pp. 119-125.

(Continued)

*Primary Examiner* — Benjamin P Blumel
(74) *Attorney, Agent, or Firm* — Millen, White, Zelano & Branigan, P.C.

(57) ABSTRACT

There is provided a novel method of forming uniform viral particles under physiological conditions. The method of forming uniform-sized viral particle aggregates composed of viral protein is characterized by incubating a viral protein such as SV40 virus VP1 at pH 5.0 to 7.0, room temperature, in the presence of 130 mM to 170 mM sodium chloride and 1.5 mM to 2.5 mM divalent cation, and in the presence of a particle formation acceleration factor such as SV40 VP2. For encapsulation of a substance to be encapsulated in the viral particles, the substance to be encapsulated is included during the incubation.

19 Claims, 14 Drawing Sheets

(56) References Cited

OTHER PUBLICATIONS

Christensen, Neil D. et al., "Hybrid Papillomavirus L1 Molecules Assemble Into Virus-like Particles that Reconstitute Conformational Epitopes and Induce Neutralizing Antibodies to Distinct HPV Types", Virology, 291, 2001, pp. 324-332.

Chang et al., "Self-assembly of the JC Virus Major Capsid Protein, VP1, Expressed in Insect Cells", Journal of General Virology, vol. 78, 1997, pp. 1435-1439.

Office Action issues in European application No. 05 757 912.0, dated Dec. 23, 2010.

Office Action for related Japanese Patent Application No. 2010 135520 dated Jun. 5, 2012.

Frisque et al. "Human polyomavirus JC virus genome," J. Virol. 1984, 51(2):458.

Moyne et al. "Absence of nucleosomes in a histone-containing nucleoprotein complex obtained by dissociation of purified SV40 virions," Cell, Aug. 1982;30(1):123-30.

Brady et al. "Efficient Transcription of a Compact Nucleoprotein Complex Isolated from Purified Simian Virus 40 Virions," J Virol. Aug. 1980; 35(2): 371-381.

JP2010-135520 (Official Abstract of JP2010-135520 (available from Patent Abstracts of Japan)).

Goldman et al. ("Molecular Cloning and Expression of Major Structural Protein VP1 of the Human Polyomavirus JC Virus: Formation of Virus-Like Particles Useful for Immunological and Therapeutic Studies," J Virol. May 1999; 73(5): 4465-4469).

Abstract "Study of Foreign Gene Delivery System with Capsid Protein VP1 of JC Virus," Proceedings of the Japanese Society of Pathology, 91 (1), 253, 2002).

* cited by examiner

Fig.1
pH4
50nm
pH5
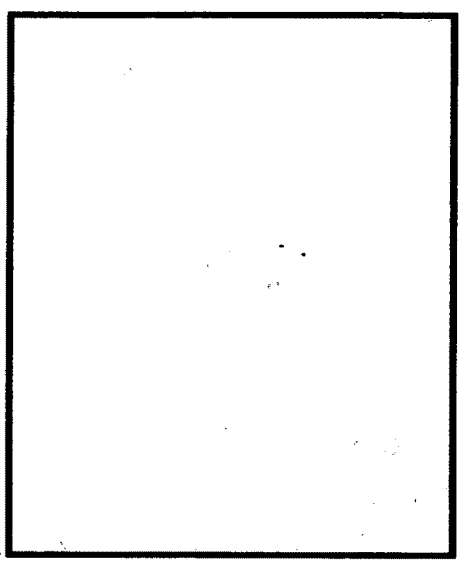
50nm
pH6
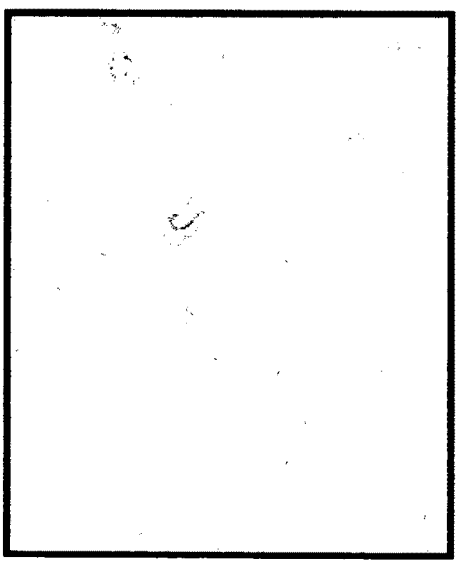
50nm
pH7
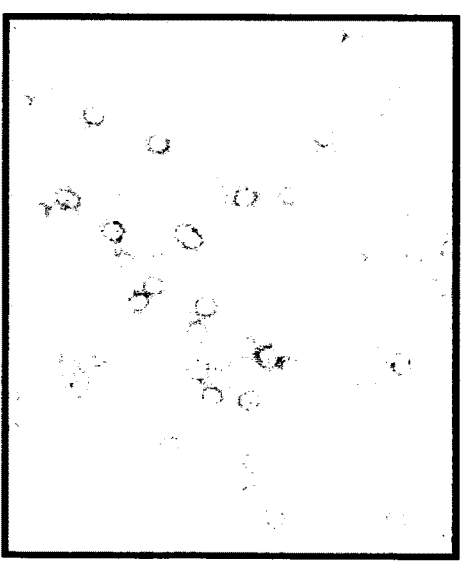
50nm

Fig.2
pH4
50nm
pH5
50nm
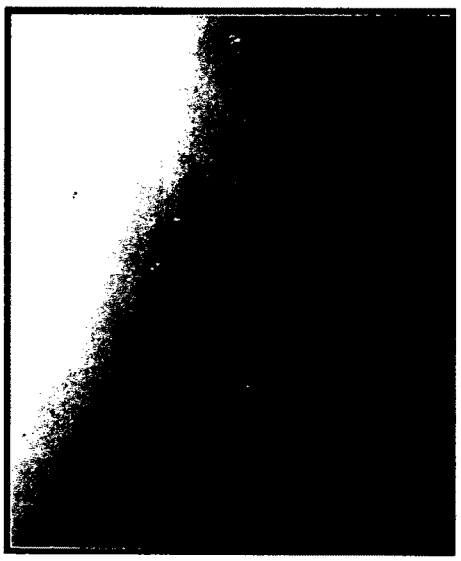
pH6
50nm
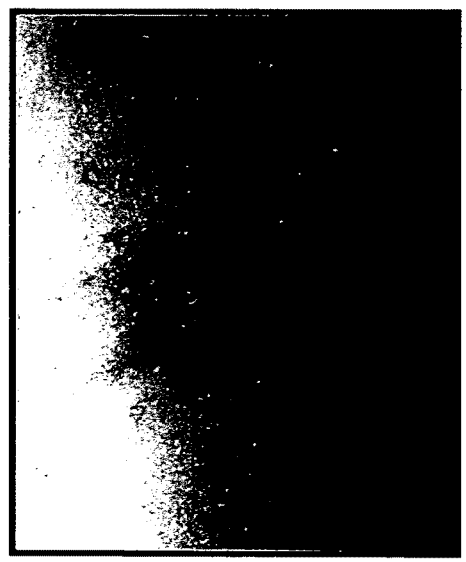
pH7
50nm

Fig. 3
VP1:VP2, 360:10.5
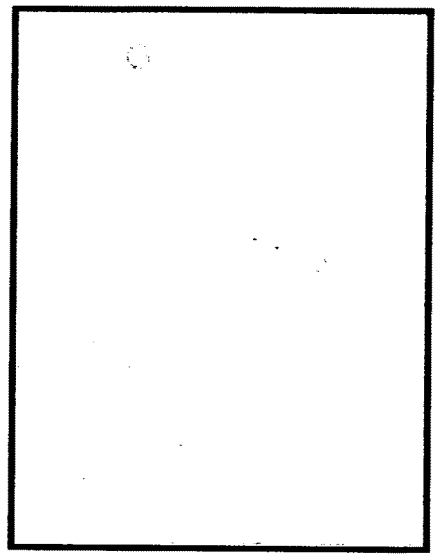
50nm
VP1:VP2, 360:21
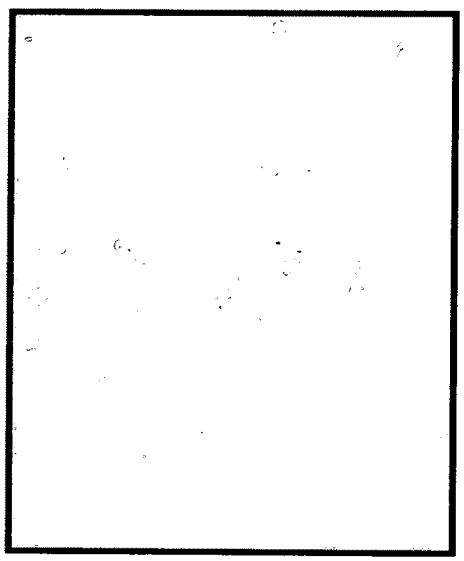
50nm
VP1:VP2, 360:42
50nm
VP1:VP2, 360:84
50nm Fig.4
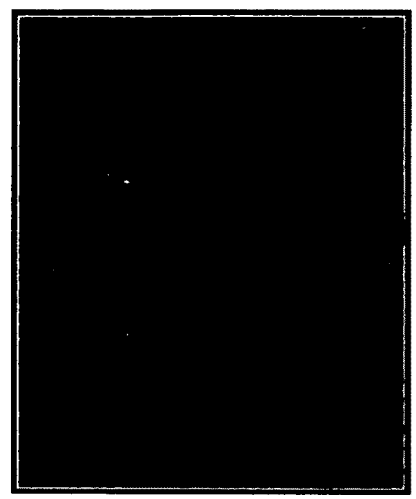
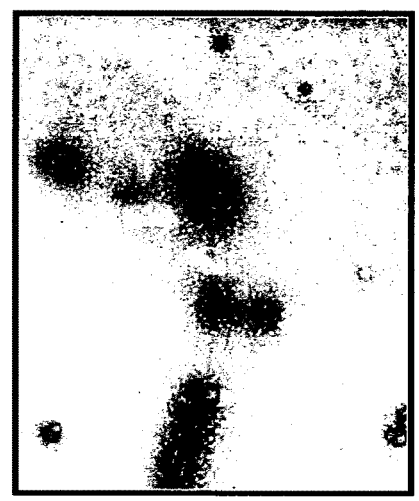
ΔC40VP2          ΔC80VP2
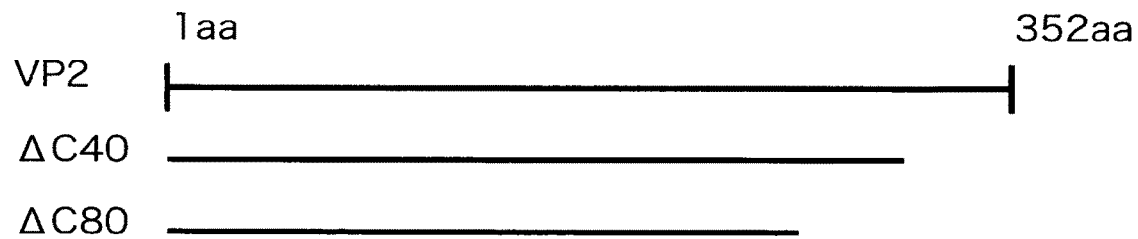

Fig.5

PGG→RER

LPLLL→APLLA

50nm

50nm

FI→AA

FI→EE

50nm

50nm

```
         1aa                              352aa
VP2  |----------------------|+++|----------|
                          276aa
         |-------------------|-----------|  FI→AA
                          276aa
         |-------------------|-----------|  FI→EE
                              283aa
         |----------------------|--------|  PGG→RER
                                  296aa
         |-------------------------|-----|  LPLLL→APLLA
```

Fig.13
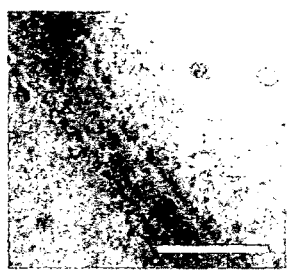
VP1 : DNA = 360 : 0
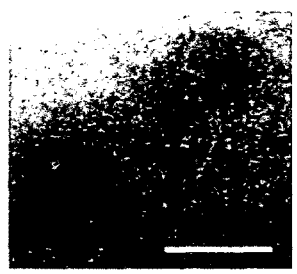
360 : 10
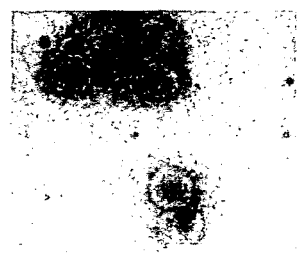
360 : 20
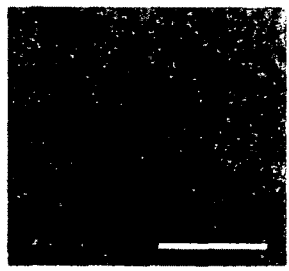
360 : 50
360 : 100
SCALE BAR 100nm
TEM Mag 200,000 ×

Fig.14
 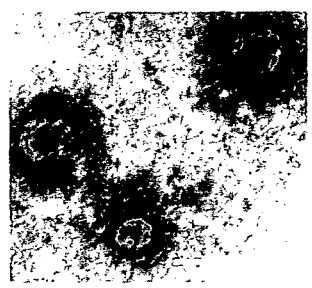
VP1 : 10μg
total RNA : 741ng
RNase +
VP1 : 10μg
total RNA : 741ng
RNase −
SCALE BAR:100nm

VIRAL PARTICLE-LIKE STRUCTURE IN PHYSIOLOGICAL CONDITIONS, AND METHOD OF FORMING IT This application is a continuation of U.S. patent application Ser. No.: 11/630,954, filed Dec. 28, 2006 now abandoned, which is a national phase of PCT/JP05/12524, filed Jun. 30, 2005, both of which are incorporated by reference herein.

SEQUENCE LISTING

The instant application contains a Sequence Listing which has been submitted in ASCII format via EFS-Web and is hereby incorporated by reference in its entirety. Said ASCII copy, created on Jan. 28, 2013, is named SEIWA22C.txt and is 19,622 bytes in size.

TECHNICAL FIELD

The present invention relates to a viral particle-like structure comprising viral protein, and to a method of forming it. The viral particle-like structure can encapsulate other substances within it, and therefore has potential use as a carrier for drug delivery and gene therapy.

BACKGROUND ART

Conventional formation of viral particle-like structures has involved recovering virus-like particles formed within cells.

In some methods, the virus-like particles are purified from the cells and are first dissociated into particle structure units (for example, VP1 pentamers in the case of SV40 virus), and then reconstituted into virus-like particles in a test tube.

Conventional reconstituting methods have been conducted under non-physiological conditions with high salt concentration, but because of problems such as inactivation or poor solvent solubility of bioactive substances included in the particles, the conditions have not been suitable for taking up bioactive substances into particles. Moreover, it has been difficult to efficiently reconstitute virus-like particles of uniform size by such methods.

DISCLOSURE OF THE INVENTION

The present invention provides a method which allows a viral particle-like structure to be reconstituted in a test tube to form uniform-sized particles efficiently and under physiological conditions.

The invention further provides a method for forming a viral particle-like structure in host cells.

The object of the invention, of forming uniform-sized virus-like particles efficiently under physiological conditions in a test tube, is achieved by adding to the reconstituting environment a protein that is found in natural viral particles.

Thus, the invention provides a uniform-sized viral particle-like structure composed of a viral protein and a particle formation acceleration factor. The invention further provides a uniform-sized viral particle-like structure composed of a viral protein and a particle formation acceleration factor, which houses a substance to be encapsulated.

The invention still further provides a method of forming a uniform-sized particle aggregate composed of viral protein and a particle formation acceleration factor, characterized by incubating the viral protein at pH 5 to 10.0, room temperature, in the presence of 130 mM to 500 mM monovalent cation and 2 μM to 50 mM divalent cation, and in the presence of the particle formation acceleration factor; and a method of forming a uniform-sized viral particle-like structure composed of a substance to be encapsulated and a viral protein surrounding it, with a particle formation acceleration factor, characterized by incubating the viral protein and substance to be encapsulated at pH 5 to 10.0, room temperature, in the presence of 130 mM to 500 mM monovalent cation and 2 μM to 50 mM divalent cation, and in the presence of the particle formation acceleration factor.

The invention still further provides a method of introducing a bioactive substance into virus-like particles composed of viral protein and capsid protein VP2 or a portion thereof, characterized by coexpressing in host cells the viral protein and capsid protein VP2 or a portion thereof comprising the binding region of the viral protein and having a bioactive substance linked thereto.

The invention still further provides a method for producing viral particle aggregates composed of viral protein encapsulating a polymer with a negatively charged surface, the method being characterized by mixing the viral protein with the polymer at 0.01 to 100 parts (by weight) with respect to 360 parts of the viral capsid protein, and dialyzing the mixture against an aqueous solution containing a monovalent metal salt and a divalent metal salt.

The negatively charged polymer is preferably DNA, RNA or a synthetic nucleic acid-like structure. In the method for producing viral particle aggregates, the weight ratio of the viral protein and the negatively charged polymer added to 360 parts of the viral capsid protein is preferably 0.2 part or greater.

The viral protein of the viral particle-like structure is preferably VP1 capsid protein of SV40 virus, JC virus or BK virus.

As SV40 viral proteins there may be mentioned VP1 capsid protein and its mutant forms. Examples of VP1 capsid protein mutants include a protein which is VP1 capsid protein having the amino acid sequence listed as SEQ ID NO: 2 with a deletion, addition or amino acid substitution of one or more amino acids. Examples of specific substitutions include at least one amino acid substitution from among Glu at position 49, Glu at position 51, Glu at position 160, Glu at position 163, Ser at position 216, Lys at position 217, Glu at position 219, Glu at position 332, Glu at position 333 and Asp at position 348 of the amino acid sequence listed as SEQ ID NO: 2.

The particle formation acceleration factor of the viral particle-like structure is preferably the viral particle capsid protein, the N-terminal region of the protein having particle formation accelerating activity, or a protein which is modified with a deletion, addition and/or amino acid substitution of one or more amino acids of the protein and which retains particle formation accelerating activity. The viral particle capsid protein is preferably the capsid protein VP2 of SV40 virus, JC virus or BK virus. As a more specific example, the viral particle capsid protein may be capsid protein VP2 of SV40 virus having the amino acid sequence listed as SEQ ID NO: 1.

When the virus-like structure of the invention is formed in vitro, such as in a test tube, preferably the viral particle capsid protein is a portion of SV40 viral capsid protein VP2 comprising at least the amino acid sequence from residues 1 to 272, or at least the amino acid sequence from residues 1 to 58, 59 to 118, 119 to 152 or 153 to 272 of the amino acid sequence listed as SEQ ID NO: 1.

When the virus-like structure of the invention is formed in host cells, preferably the viral particle capsid protein is a portion of SV40 viral capsid protein VP2 comprising at least the amino acid sequence of the VP1-binding region from residues 273 to 307 of the amino acid sequence listed as SEQ ID NO: 1, and preferably it is linked to the desired bioactive substance or non-bioactive substance to be introduced, or a combination thereof.

The non-bioactive substance is, for example, a low molecular substance or high-molecular substance, or a combination thereof.

The factor to be encapsulated will typically be a bioactive substance, and for example, may be a nucleic acid, protein or low molecular substance.

The monovalent cation forming the viral particle-like structure of the invention is preferably sodium ion, and it may be used in the form of sodium chloride. The divalent cation forming the viral particle-like structure of the invention is preferably calcium ion, and it may be used in the form of calcium chloride. The concentration of the monovalent cation may be, for example, 150 mM, and the concentration of the divalent cation may be, for example, 2 mM.

The invention also relates to a composition for introduction of a bioactive substance into cells, whose active component is the aforementioned viral structure comprising a bioactive molecule.

BRIEF EXPLANATION OF THE DRAWINGS

FIG. 1 is a set of electron microscope photographs showing a viral particle-like structure formed by the method of the invention in the presence of a particle formation acceleration factor.

FIG. 2 is a set of electron microscope photographs showing viral protein treated under physiological conditions in the absence of a particle formation acceleration factor.

FIG. 3 is a set of electron microscope photographs showing formation of viral particle-like structures upon changing the proportion of viral protein VP1 and particle formation acceleration factor VP2.

FIG. 4 is a pair of electron microscope photographs showing viral particle-like structures produced using particle formation acceleration factor VP2 lacking the C-terminal end.

FIG. 5 is a set of electron microscope photographs showing viral particle-like structures produced using particle formation acceleration factor VP2 having a point mutation introduced at the C-terminal end. FIG. 5 discloses 'LPLLL' as SEQ ID NO: 3 and 'APLLA' as SEQ ID NO: 4.

FIG. 13 is a set of photographs showing the results of electron microscope observation of the product obtained in Example 6.

FIG. 14 is photograph showing reconstitution by mixing RNase pre-treated total RNA, RNase untreated total RNA and purified VP1 protein and dialyzing the mixture in a pH 5, 150 mM NaCl, 2 mM CaCl$_2$ solution for 16 hours at room temperature, in Example 7. After reconstitution, an electron microscope was used for observation of the aggregated VP1 pentamers in exchanged solvent. This photograph shows the RNase-treated RNA as RNase+ and the RNase-untreated RNA as RNase−. It suggests that formation of globular virus-like particles occurs due to the presence of RNA.

BEST MODE FOR CARRYING OUT THE INVENTION

Figure 6:
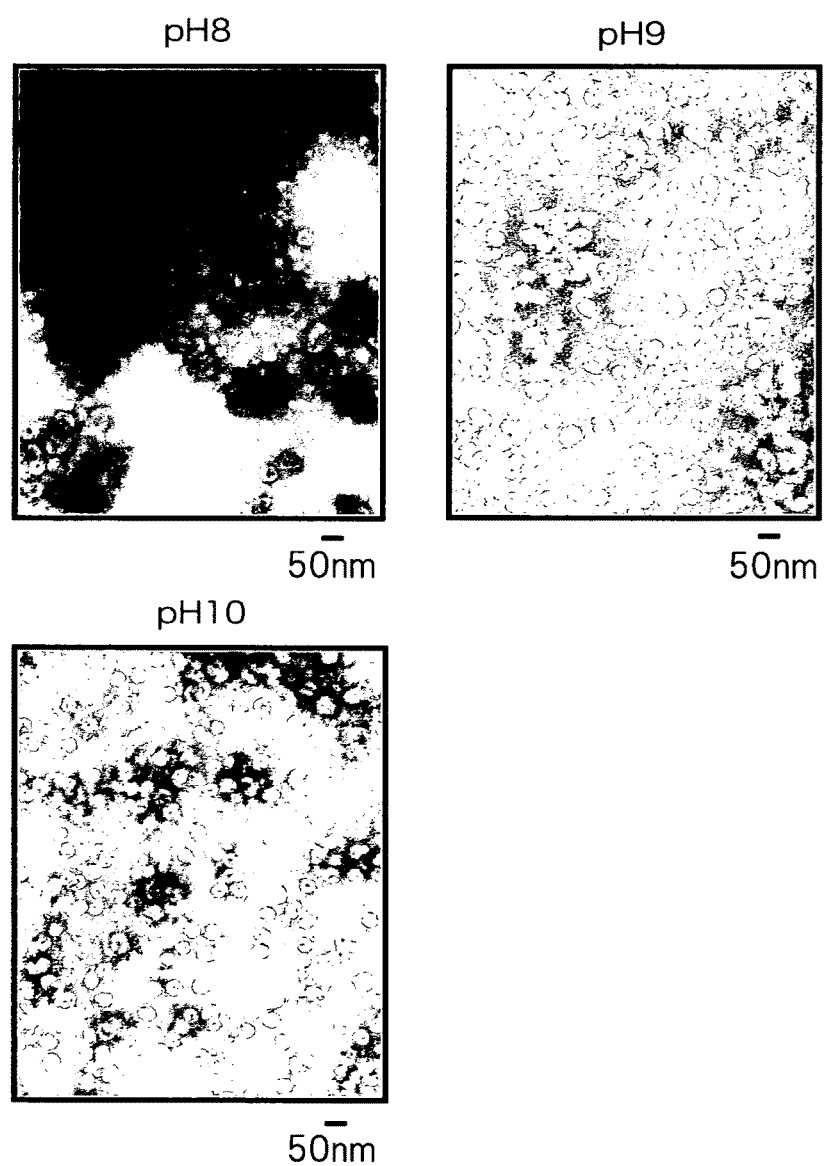
FIG. 6 is a set of electron microscope photographs showing that uniform globular viral particle-like structures are formed even in the absence of a particle formation acceleration factor when incubation is performed under non-physiological conditions of pH 8 to 10.

According to the invention, viruses that may be used as protein sources for formation of viral protein particles are not particularly restricted so long as particles can be formed from the major constituent protein or particle outer shell constituent protein. As examples of major constituent proteins there may be mentioned those of Simian virus 40 (SV40), human polyoma virus JC, and BK virus. SV40 VP1 is particularly preferred. As an example of a particle outer shell forming protein there may be mentioned the capsid protein VP1 (of SV40 or the human polyoma viruses JC virus and BK virus) or the like.

The SV40 VP1 may be naturally occurring VP1 or a mutant thereof. Examples of mutants include VP1 capsid protein having the amino acid sequence listed as SEQ ID NO: 2 with a deletion, addition or amino acid substitution of one or more amino acids, and specific substitutions include at least one amino acid substitution from among Glu at position 49, Glu at position 51, Glu at position 160, Glu at position 163, Ser at position 216, Lys at position 217, Glu at position 219, Glu at position 332, Glu at position 333 and Asp at position 348 of the amino acid sequence listed as SEQ ID NO: 2.

According to one mode, the invention provides a protein (mutant A; mtA) wherein Glu at position 160 is replaced by another amino acid, and which can form more rigid or stable virus-like protein particles than the wild type. This Glu is preferably replaced by Gln.

According to another mode, the invention provides a protein (mutant B; mtB) wherein Glu at position 163 is replaced by another amino acid, and which forms more rigid or stable virus-like protein particles than the wild type. This Glu is preferably replaced by Gln.

According to yet another mode, the invention provides a protein (mutant C; mtC) wherein Asp at position 348 is replaced by another amino acid, and which forms more rigid or stable virus-like protein particles than the wild type. This Asp is preferably replaced by Asn.

According to yet another mode, the invention provides a protein (mutant D; mtD) wherein Glu at position 160 and Glu at position 163 are replaced by other amino acids, and which forms more rigid virus-like protein particles than the wild type. This Glu is preferably replaced by Gln.

According to yet another mode, the invention provides a protein (mutant E; mtE) wherein Glu at position 160, Glu at position 163 and Asp at position 348 are replaced by other amino acids, and which forms more rigid or stable virus-like protein particles than the wild type. The Glu is preferably replaced by Gln, and Asp is preferably replaced by Asn.

According to yet another mode, the invention provides a protein (mutant F; mtF) wherein Glu at position 332, Glu at position 333 and Asp at position 348 are replaced by other amino acids, and which forms rod-shaped virus-like protein particles at high incidence. The Glu is preferably replaced by Gln, and Asp is preferably replaced by Asn.

According to yet another mode, the invention provides a protein (mutant G; mtG) wherein Glu at position 49 and Glu at position 51 are replaced by other amino acids, and which forms more rigid or stable virus-like protein particles than the wild type. The Glu is preferably replaced by Gln.

According to yet another mode, the invention provides a protein (mutant H; mtH) wherein Glu at position 49, Glu at position 51, Glu at position 160, Glu at position 163, Ser at position 216, Lys at position 217, Glu at position 219, Glu at position 332, Glu at position 333 and Asp at position 348 are replaced by other amino acids, and which does not form virus-like protein particles as easily as the wild type. The Glu is preferably replaced by Gln, the Asp is preferably replaced by Asn, the Ser is preferably replaced by Ala and the Lys is preferably replaced by Ala.

A method of preparing such mutants is described in detail in Japanese Unexamined Patent Publication No. 2002-360266.

According to the invention, it is necessary to use the particle formation acceleration factor under conditions of pH 5 to 10. The particle formation acceleration factor is preferably, for example, a viral particle protein. As examples of viral particle proteins there may be mentioned capsid protein VP2 of SV40 virus, JC virus or BK virus, or its N-terminal portion, or histone protein or the like. Particularly preferred as a viral particle protein is SV40 VP2 or its N-terminal portion. The amino acid sequence of SV40 VP2 is listed as SEQ ID NO: 1. When SV40 VP2 or a portion thereof is used as the particle formation acceleration factor for the invention to form a virus-like structure in vitro, it need only comprise at least the amino acid sequence from the amino acid at position 1 to the amino acid at position 58, the amino acid sequence from the amino acid at position 59 to position 118, the amino acid sequence from positions 119 to 152 and the amino acid sequence from positions 153 to 272, of the amino acid sequence listed as SEQ ID NO: 1.

When SV40 virus capsid protein VP2 is used to form the virus-like structure in cells, the capsid protein need only comprise at least the amino acid sequence of the VP1-binding region from positions 273 to 307 of the amino acid sequence listed as SEQ ID NO: 1.

The viral particle protein of the invention may have, for example, the amino acid sequence listed as SEQ ID NO: 1 or its N-terminal sequence modified by an addition, deletion and/or amino acid substitution of one or more amino acid residues, while still retaining particle formation acceleration factor activity. The number of amino acid residues modified may be, for example, 1 to 20, 1 to 15 or one to a few.

The concentration of the viral protein forming the outer shell of the particles is 50 ng/μL to 500 ng/μL and preferably 70 ng to 200 ng, and the concentration of protein as the particle formation acceleration factor is 1 ng/μL to 1 μg/μL and preferably 10 ng/μL to 100 ng/μL. The concentration of the substance to be encapsulated, for encapsulation into the viral particles, will differ depending on the type of substance but may be 0.1 ng/μL to 10 μg/μL and preferably 10 ng/μL to 1 μg/μL.

According to the invention, the viral protein may be incubated (1) in a pH range of pH 5 to 10, (2) at room temperature and in the presence of (3) 130 mM to 500 mM monovalent cation, (4) 2 μM to 50 mM divalent cation and (5) a particle formation acceleration factor, to form globular, uniform-sized particles. Sodium is preferred as the monovalent cation, such as in the form of sodium chloride, and the concentration of sodium ion is preferably 140 mM to 160 mM and especially 150 mM.

As divalent cations there may be used calcium ion, cadmium ion, manganese ion, magnesium ion and zinc ion, but calcium ion is particularly preferred, and for example, calcium chloride may be used. The concentration of calcium ion is preferably 1.75 mM to 2.25 mM, and especially 2 mM.

Incubation in a range of pH 8 to 10 at room temperature in the presence of 130 mM to 170 mM sodium chloride, 1.5 mM to 2.5 mM divalent cation can form globular uniform-sized viral particle-like structures without addition of a particle formation acceleration factor.

In the method for formation of viral particles encapsulating a substance to be encapsulated according to the invention, the substance to be encapsulated may be included during the incubation for formation of the viral particles. There are no particular restrictions on the substance to be encapsulated, and for example, there may be mentioned nucleic acid, i.e. DNA or RNA, and especially DNA, proteins or peptides, and various low molecular substances such as pharmaceutically active substances.

The viral structure comprising the bioactive molecule prepared in the manner described above may be used for introduction of the bioactive substance into cells. This will allow application for introduction of the bioactive substance into viable cells for the purpose of drug delivery, gene therapy or the like, in the field of regenerative therapies employing gene transfer, gene therapy, targeted gene expression and functional suppression, or application for tissue- and organ-specific or lesion-specific labeling methods using virus-like particles containing labeled substances and the like.

EXAMPLES

The present invention will now be explained in greater detail by examples.

Example 1

Preparation of Viral Particles (1) Preparation of viral particle (VP1) pentamers After seeding Sf9 cells at $1 \times 10^7$ each into fifty 10 cm-diameter tissue culturing dishes, they were infected with recombinant baculovirus expressing SV40 viral protein (VP1) with a m.o.i. (multiplicity of infection) of 5 to 10.

At 72 hours after infection, the cells were recovered with medium using a scraper, and rinsed twice with cooled phosphate buffered saline (PBS). To the recovered cells there was added 10 mL of ice-cooled sonication buffer (20 mM Tris-HCl (pH 7.9), 1% (w/v) sodium deoxycholate (DOC), 2 mM PMSF), and then a VP-15S (sonicator) by Taitec was used for 10 minutes of ultrasonic disruption while cooling on ice under conditions with a 50% duty cycle and output at 5. The cell disruptate was centrifuged at 14,000 g, 4° C. for 20 minutes and the supernatant was recovered.

Cesium chloride solutions with four different densities (50%, 40%, 30%, 20% (w/v)) were gently layered at 1.5 ml each in a SW41Ti Open Top Ultraclear Tube (Beckman) in order from the highest density, and then 5 mL of the cell disruptate was layered thereover and centrifugation was performed for 2.5 hours with a SW41Ti Rotor (Beckman) at 30,000 rpm, 4° C. After centrifugation, the white SV40 virus-like particle (VLP) layer formed midway in the density gradient was collected. The collected solution was transferred to an SW55Ti Open Top Ultraclear Tube (Beckman), a 37% (w/v) cesium chloride solution was added to approximately 5 mm from the tip of the volume tube, and the mixture was centrifuged for 20 hours with an SW55Ti Rotor (Beckman) at 50,000 rpm, 4° C. after which the re-formed VLP layer was recovered.

To the obtained purified viral protein solution there was added a 1/100 volume of 10% (v/v) surfactant NP-40 (final concentration: 0.1%), and the mixture was dialyzed for 24 hours at 4° C. in a dialyzing solution containing 20 mM Tris-HCl (pH 7.9), 0.1% NP-40 for removal of the cesium chloride. Dialysis was followed by centrifugation for 10 minutes at 15,000 g, 4° C., and the supernatant was collected.

Next, 0.25 Methylene glycol bis(β-aminoethyl ether)-N,N, N',N'-tetraacetate (EGTA) and 1 M dithiothreitol (DTT) were added to the virus-like particles to respective final concentrations of 25 mM EGTA and 30 mM DTT, and incubation was performed at 37° C. for 1 hour to dissociate the virus-like particles into VP1 pentamers. Incubation was followed by centrifugation for 10 minutes at 15,000 g, 4° C., and the obtained supernatant was subjected to gel filtration chromatography for purification of the VP1 pentamers. The chromatography was carried out using a HiLoad 16/60 Superdex 200 pg column (Pharmacia) under conditions of 20 mM Tris-HCl (pH 7.9), 150 mM NaCl, 5 mM EGTA, 5 mM DTT, 4° C.

A portion of each obtained fraction was taken and subjected to SDS polyacrylamide gel electrophoresis, protein detected at a molecular weight of about 200 kDa was considered to be VP1 pentamer, and the fraction containing the protein was considered to be the VP1 pentamer-containing fraction and was frozen with liquid nitrogen and then stored at −80° C.

(2) Preparation of SV40-VP2 protein

The SV40-VP2 gene having the histidine sequence and FLAG sequence inserted at the amino terminal end was incorporated into pET-14b vector for transformation of $E.$ $coli$ BL21. The transformed $E.$ $coli$ was inoculated into 250 ml of LB medium and shake cultured at 37° C. When the culture solution reached the logarithmic growth stage (turbidity: O.D. value=0.3 (wavelength: 660 nm)), protein expression was induced with IPTG. At four hours after induction of expression, the $E.$ $coli$ cells were centrifuged and collected and then rinsed twice with cooled phosphate buffered saline (PBS). To the recovered $E.$ $coli$ cells there was added 40 ml of ice-cooled binding buffer (20 mM Tris-HCl (pH 7.9), 10% glycerol, 500 mM KCl, 0.2 mM EDTA, 0.1% NP-40, 0.5 mM DTT, 10 mM imidazole), and a VP-15S (sonicator) by Taitec was used for 10 minutes of ultrasonic disruption while cooling on ice under conditions with a 50% duty cycle and output at 5. The cell disruptate was then centrifuged for 20 minutes at 14,000 g, 4° C. and the supernatant was collected.

The collected supernatant was mixed with 500 μL of H is resin (Qiagen) that had been equilibrated with binding buffer, and the mixture was stirred by slowly rotating with a rotor for one hour at 4° C. The stirred solution was centrifuged to convert the resin to a pellet, and the supernatant was removed. After adding 10 mL of wash buffer (20 mM Tris-HCl (pH 7.9), 10% glycerol, 500 mM KCl, 0.2 mM EDTA, 0.1% NP-40, 0.5 mM DTT, 20 mM imidazole) to the resin, the mixture was stirred. The stirred solution was again centrifuged and the supernatant was carefully removed. This washing procedure was repeated 3 times. Finally, 500 μL of elution buffer (20 mM Tris-HCl (pH 7.9), 10% glycerol, 500 mM KCl, 0.2 mM EDTA, 0.1% NP-40, 0.5 mM DTT, 1M imidazole) was added to the resin and the mixture was stirred. The stirred solution was centrifuged and the supernatant was carefully collected. This procedure was repeated twice to obtain a total of 1 ml of SV40-VP2 protein.

(3) in vitro reconstitution of viral particles under physiological conditions

The prepared SV40-VP1 protein pentamers and SV40-VP2 protein were used for in vitro reconstitution of viral particles under physiological conditions. Specifically, for pH 5 to 7, 3.4 μl of 800 ng/μL VP2 protein was added to 150 μL of 82.5 ng/μL VP1 pentamer protein, incubation was performed at 4° C. for 30 minutes, and the mixture was dialyzed by a dialysis method with a solution containing 150 mM NaCl, 2 mM CaCl$_2$ for reconstitution. The addition was to a molar ratio of VP1 protein and VP2 protein of 360:84. Detection of viral-like particles was accomplished by electron microscope observation. The results are shown in FIG. 1.

(4) Examination of VP1 pentamer assembly under physiological conditions

A solution containing the purified VP1 pentamer protein was solvent-exchanged under physiological conditions, and the state of aggregation was examined. Unlike the results of (3) in which particle formation was observed, in this case when the pH was 5.0 to 7.0 under physiological conditions, almost no viral particle-like structure formation was seen with VP1 pentamer alone. VP1, for example, 150 μL of VP1 pentamer at 270 ng/μL concentration, was dialyzed at room temperature with a solution of 150 mM NaCl, 2 mM CaCl$_2$ at pH 4, 5, 6 or 7. After 16 hours from the start of dialysis, the solution was recovered and observed under an electron microscope, and the state of aggregation of VP1 pentamers under different conditions was observed. The results are shown in FIG. 2.

(5) Aggregation with addition of VP2 protein to VP1 pentamer at varying proportions under physiological conditions Protein solution was added to purified VP1 pentamer protein at molecular weight ratios of VP1 protein:VP2 protein=360:10.5, 360:21, 360:42 and 360:84. The solution was solvent-exchanged under physiological conditions at pH 5.0 at room temperature using a dialysis method. The exchanged solvent was observed under an electron microscope to examine the state of aggregation seen when varying the VP2 protein concentration.

For example, protein solutions were mixed with 150 μL of VP1 pentamer at 270 ng/μL concentration and 1.1 μL, 2.2 μL, 4.4 μL and 8.8 μL of VP2 protein at 1.1 μg/μL concentration. The solution was incubated at 4° C., 30 min and dialyzed for 16 hours at room temperature with a pH 5, 150 mM NaCl, 2 mM CaCl$_2$ solution. The solution was recovered and observed under an electron microscope to observe the state of aggregation of VP1 pentamers with varying VP2 protein concentration. The results are shown in FIG. 3. Characteristic rod-shaped structures were seen under these pH conditions in several of the experiment groups, but globular virus-like particles were simultaneously formed.

(6) Aggregation of VP1 pentamers with addition of ΔC13 VP2 protein, ΔC40 VP2 protein and ΔC80 VP2 protein lacking carboxyl terminal ends Purified VP1 pentamer protein and purified ΔC40 VP2 protein (molecular weight: approximately 34 kDa) and ΔC80 VP2 protein (molecular weight: approximately 30 kDa) were combined in a molecular weight ratio of PV1:carboxyl terminal-lacking VP2=360:84, and the mixture was incubated at 4° C. for 30 minutes. The mixture was dialyzed at room temperature with a pH 5.0, 150 mM NaCl, 2 mM CaCl$_2$ solution.

For example, 2.6 μL of ΔC40 VP2 at 763 ng/μL concentration or 2.3 μL of ΔC80VP2 at 758 ng/μL concentration was added to 150 μL of VP1 at 75.7 ng/μL concentration, and the mixture was incubated for 30 minutes at 4° C. The mixture was dialyzed for 16 hours at room temperature using the aforementioned solution, and then the mixture was recovered and observed under an electron microscope to examine the state of aggregation of VP1 pentamers with addition of carboxyl terminal-lacking VP2 protein. The results are shown in FIG. 4. It is seen that virus-like particle formation can be induced despite the absence of a portion of the VP2 amino acid sequence.

(7) Observation of VP1 pentamer assembly with addition of point mutation-introduced VP2 protein VP1 pentamer protein was mixed with VP2 protein having different point mutations, specifically, VP2 protein having the Pro, Gly, Gly from positions 283 to 285 mutated to Arg, Glu, Arg (hereinafter, PGP→RER), the Phe at position 276 and Ile at position 277 mutated to Glu (hereinafter, FI→EE), or to Ala (hereinafter, FI→AA), and the Leu at position 296 and Leu at position 300 mutated to Ala (hereinafter, LPLLL→APLLA (SEQ ID NOS 3 and 4, respectively)), in a molecular weight ratio of VP1:point mutated VP2 =360:84, and each mixture was allowed to stand at 4° C. for 30 minutes and then dialyzed against a pH 5.0, 150 mM NaCl, 2 mM $CaCl_2$ solution at room temperature.

For example, 2.7 μL of PGP→RER VP2 at 984 ng/μL concentration, or 2.3 μL of FI→EE VP2 at 1.18 μg/μL concentration or 3.5 μL of LRLLL→ARLLA (SEQ ID NOS 5 and 6, respectively) VP2 at 779 ng/μL concentration or 2.4 μL of FI→AA VP2 at 1.13 μg/μL concentration was added to 150 μL of VP1 at 82.5 ng/μL concentration, and the mixture was allowed to stand for 30 minutes at 4° C. and dialyzed under the conditions described above. At 16 hours after the start of dialysis, the mixture was recovered and observed under an electron microscope, and the state of VP1 pentamer assembly with addition of point mutation-introduced VP2 protein was confirmed. The results are shown in FIG. 5. In all cases, there was no inhibition against the effect of virus-like particle formation by introduction of point mutations into VP2.

For example, 2.7 μL of PGP→RER VP2 at 984 ng/μL concentration, or 2.3 μL of F→EE VP2 at 1.18 μg/μL concentration or 3.5 μL of LRLLL→ARLLA VP2 at 779 ng/μL concentration or 2.4 μL of FI→AA VP2 at 1.13 μg/μL concentration was added to 150 μL of VP1 at 82.5 ng/μL concentration, and the mixture was allowed to stand for 30 minutes at 4° C. and dialyzed under the conditions described above. At 16 hours after the start of dialysis, the mixture was recovered and observed under an electron microscope, and the state of VP1 pentamer assembly with addition of point mutation-introduced VP2 protein was confirmed. The results are shown in FIG. 5. In all cases, there was no inhibition against the effect of virus-like particle formation by introduction of point mutations into VP2.

(8) Observation of VP1 pentamer assembly under conditions of pH 8.0 to pH 10.0.

Figure 7:
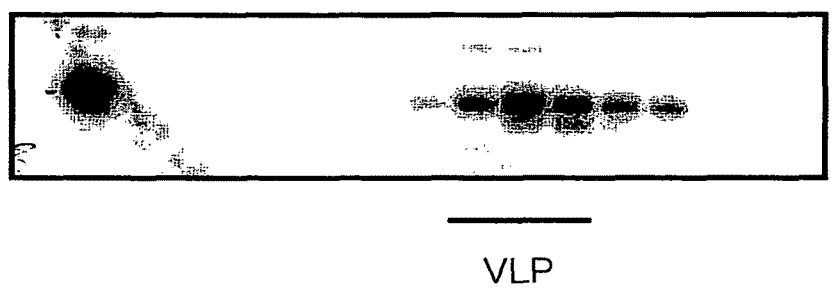
FIG. 7 is an image showing the results of fractionation by sucrose density centrifugal separation and detection by Southern blotting of the viral particles prepared in Example 2.

A solution containing purified VP1 pentamer protein was dialyzed under conditions of pH 8.0 to pH 10.0 and the state of aggregation was examined. Virus-like particle formation was observed even with VP1 pentamer alone at pH 8.0 to 10.0 under physiological conditions, unlike with the conditions of pH 5.0 to pH 7.0 necessary for particle formation acceleration factor. For example, 150 μL of VP1 pentamer at 270 ng/μL concentration was dialyzed with 150 mM NaCl, 2 mM $CaCl_2$ solutions at pH 8, 9 or 10 at room temperature. After 16 hours from the start of dialysis, the solution was recovered and observed under an electron microscope, and the state of aggregation of VP1 pentamers under different conditions was observed. The results are shown in FIG. 7.

Example 2

Formation of Virus-Like Particles Incorporating DNA

Example 1 was repeated. However, in step (3) for in vitro reconstitution of the virus-like particles under physiological conditions, a 3000 bp plasmid was included and the formed virus-like particles comprising DNA incorporated into the virus-like particles were subjected to sucrose density gradient centrifugation, and then fractionation and Southern blotting for detection of DNA. As shown in FIG. 7, the DNA was incorporated into the virus-like particles.

The prepared SV40-VP1 protein pentamers and SV40-VP2 protein were used for in vitro reconstitution of the virus-like particles under physiological conditions. DNA was added during the procedure. Specifically, at pH 5.0 to 7.0, for example, 2.8 μL of 800 ng/μL VP2 protein was added to 150 μL, of 75.7 ng/μL VP1 pentamer protein, and then 21 μL of 5.7 ng/μl 3000 bp circular double-stranded plasmid DNA (pG5vector) was added. The mixture was incubated at 4° C. for 30 minutes and dialyzed using a dialysis method with a 150 mM NaCl, 2 mM $CaCl_2$ solution for reconstitution.

Sucrose density gradient centrifugation was carried out in order to confirm detection of the DNA added to the reconstituted virus-like particle fraction. The centrifuged sample was fractionated and the fractions were subjected to protease treatment for decomposition of the VP1 protein. The sample was separated by agarose electrophoresis and subjected to Southern blotting to confirm that the DNA could be detected in the virus-like particle fraction. The virus-like particles are usually included in fractions #8, 9 and 10, and as shown in FIG. 7, detection of DNA in fractions #8, 9 and 10 confirmed that DNA had been enveloped in the virus-like particles.

Example 3

Gene Transfer into Cells Using DNA-incorporating Virus-like Particles

Example 2 was repeated. However, the plasmid used was pEG which can express a fluorescent protein (GFP) in mammalian eukaryotic cells. Formation of virus-like particles containing the pEG plasmid DNA was accomplished by sucrose density gradient centrifugation, and it was confirmed that DNA was contained in the fractions containing the virus-like particles. Specifically, the virus-like particles were reconstituted in a solvent containing 150 mM sodium chloride, 2 mM calcium chloride and 20 mM Tris HCl (pH 7.2) using VP1 and VP2 protein in the presence of the pEG plasmid, and the plasmid DNA-containing virus-like particles were fractionated by sucrose density gradient centrifugation.

Figure 8:
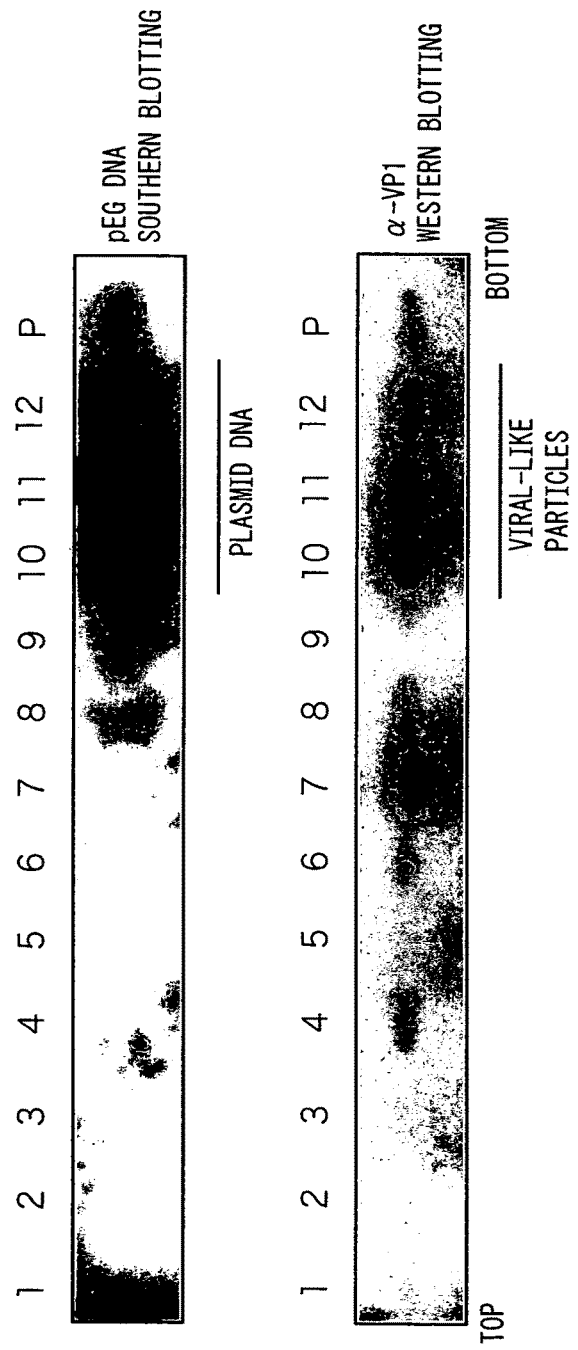
FIG. 8 is an image showing distribution of pEG DNA after fractionation of virus-like particles composed of VP1-VP2 protein in the presence of pEG by sucrose density gradient centrifugation in Example 3, and distribution of protein detected with anti-VP1 antibody.

The virus-like particles were detected by Western blotting using anti-VP1 antibody (α-VP1), and pEG was detected by Southern blotting. The results are shown in FIG. 8. The numbers in the image represent the fraction numbers, with the top density gradient listed first and the bottom listed last, and P represents the pellet that precipitated at the tube bottom during centrifugation. The fact that this DNA was resistant to treatment by the DNA lyase DNaseI suggested that it was included within the outer shell of the VP1-VP2 protein.

Figure 9:
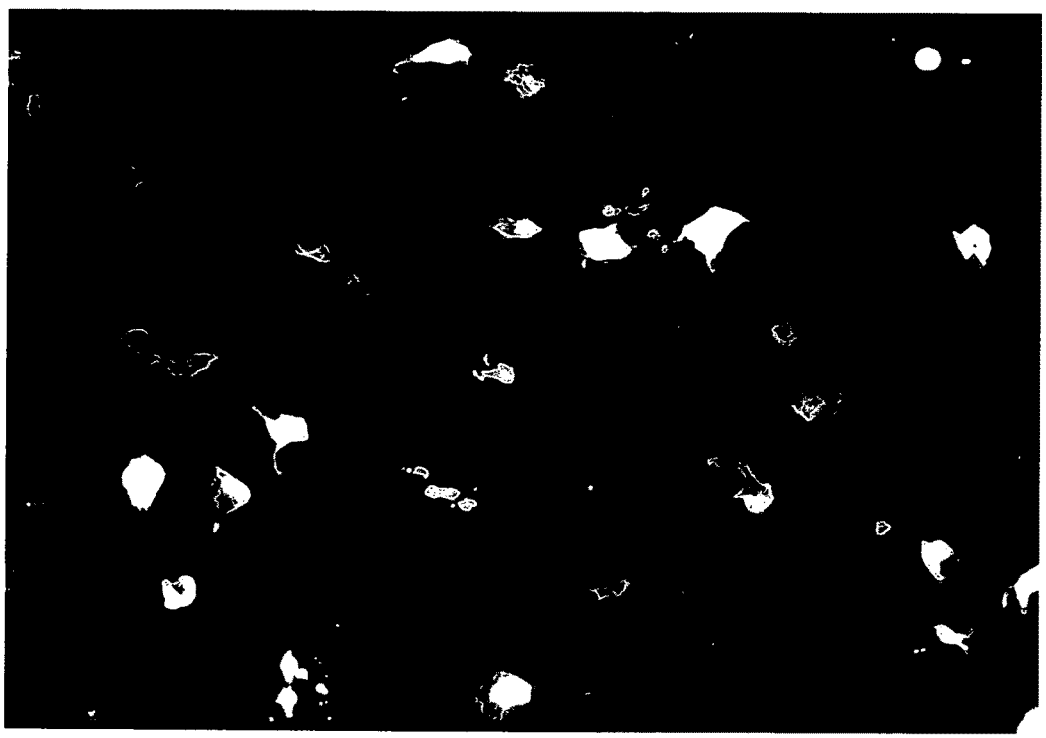
FIG. 9 is a photograph showing that pEG introduced into COS-1 cells by virus-like particles in Example 3 were expressed in cells and that fluorescent protein was produced.
Figure 10:
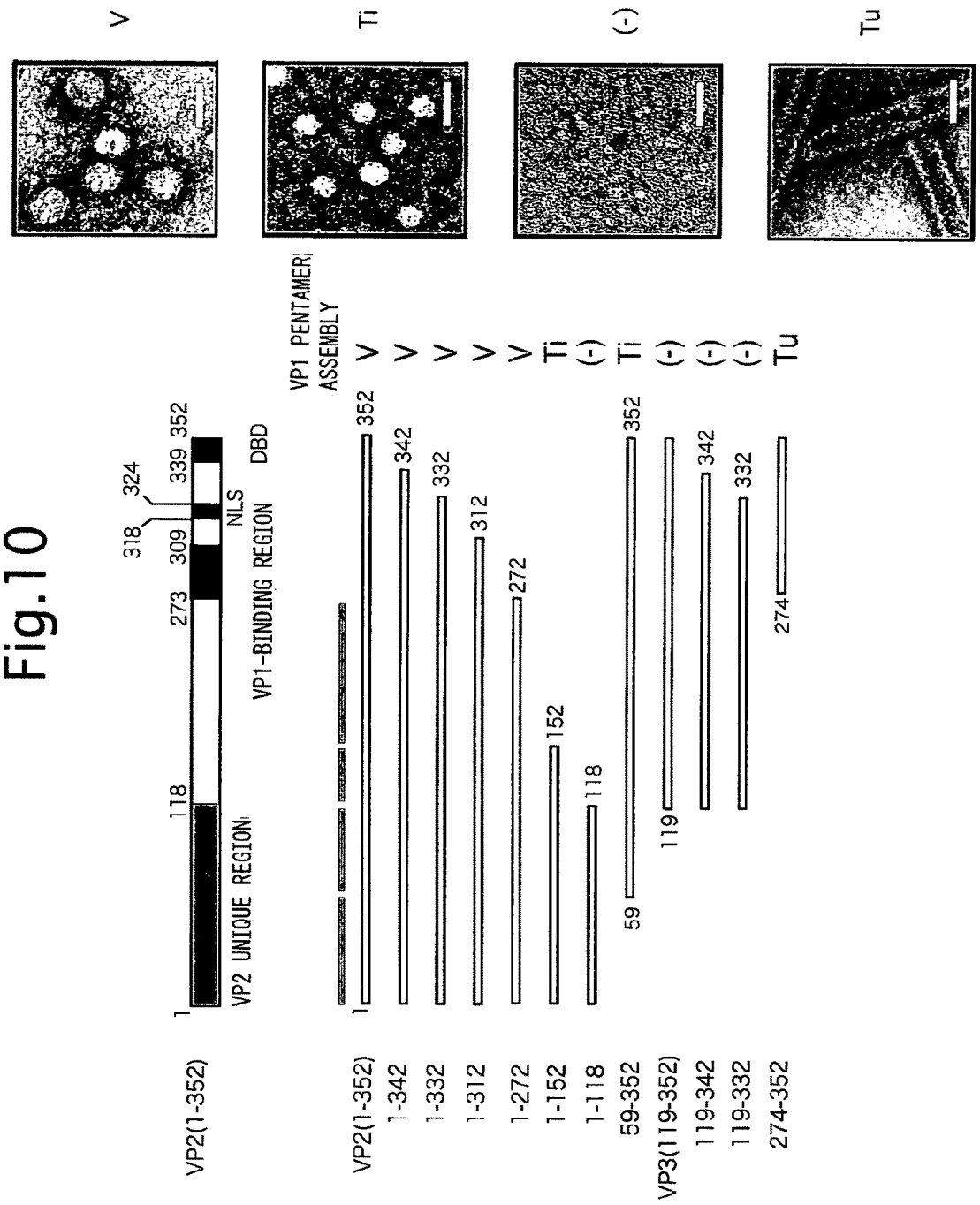
FIG. 10 is a diagram showing the results of Example 4, by the relationship between portions of VP2 protein as a particle formation acceleration factor, and virus formation.
Figure 11:
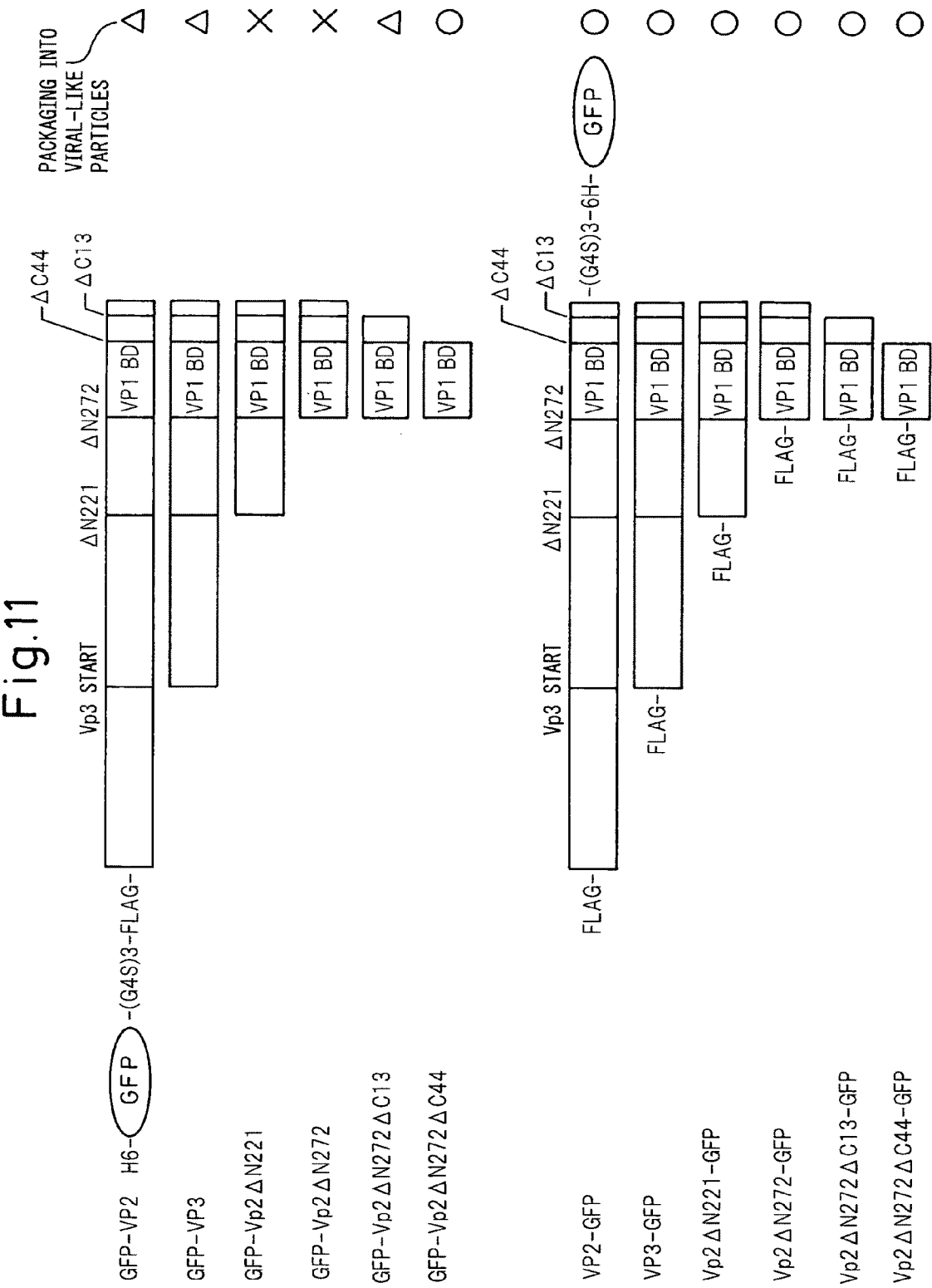
FIG. 11 is a diagram showing the results of Example 5 which indicate the portion of VP2 necessary for taking up into VP1 virus-like structures.

These virus-like particles were used for introduction of pEG DNA into COS-1 cells. Specifically, $6.65 \times 10^4$ COS-1 cells were spread on a 6 cm-diameter dish and cultured overnight. The culture solution was removed without detaching the cells, and approximately 100 µL of virus-like particles containing the aforementioned plasmid DNA were added to the cells. After incubation at 37° C. for 2 hours, the cells were wetted with culture solution every 15 minutes to avoid drying of the cells. After culturing, 1.5 mL of culture solution was added to the cells and culturing was conducted at 37° C. for 48 hours. Expression of GFP in the cells was then confirmed with a fluorescent microscope to confirm transfer of the plasmid DNA into the cells. The results are shown in FIG. 9. Expression of fluorescent protein encoded by pEG was observed in most of the cells (The indefinite shaped white sections in FIG. 9 are cells expressing fluorescent protein.), thus confirming a high rate of gene transfer by the DNA-containing viral particles.

Example 4

Figure 12:
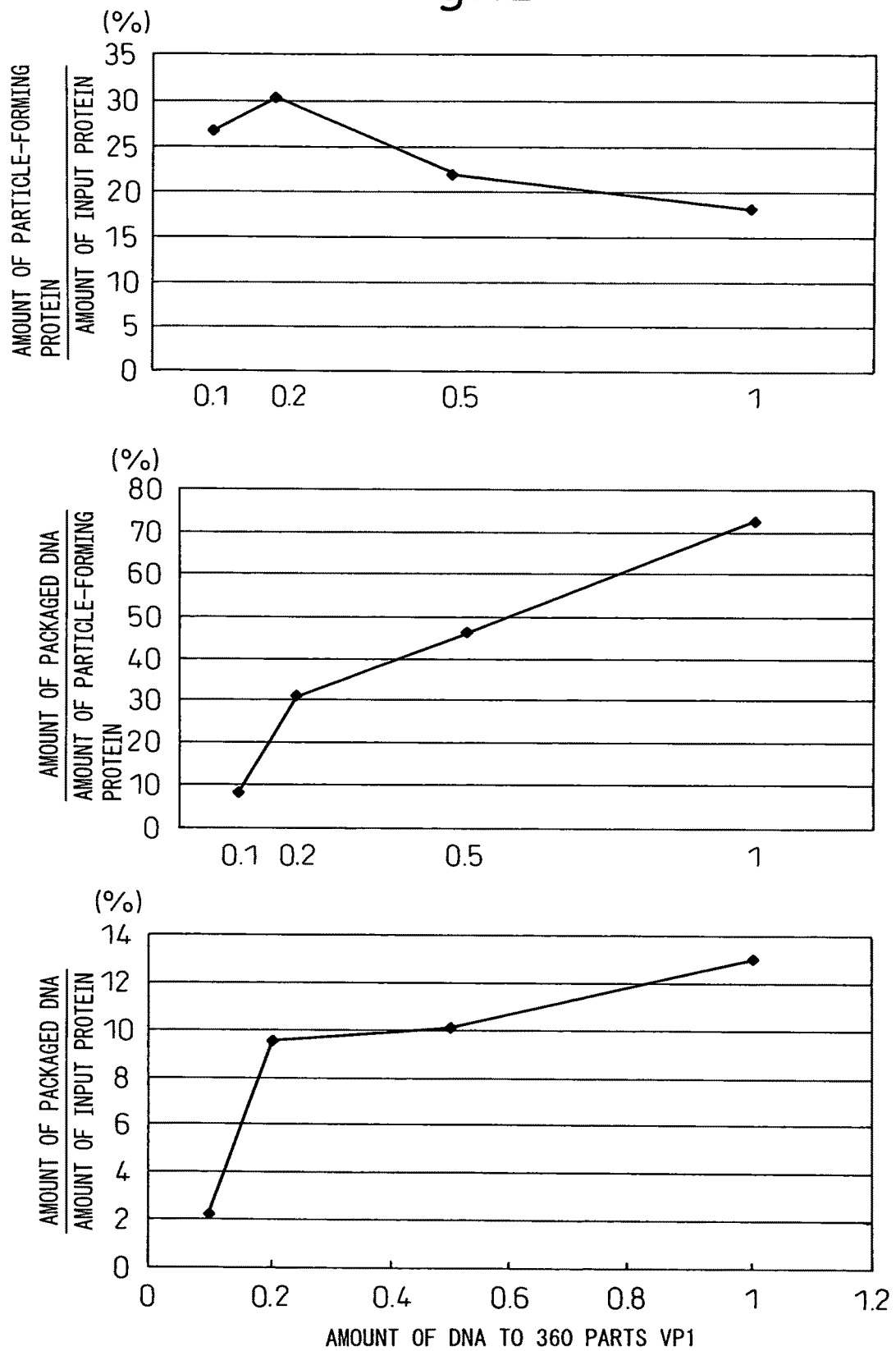
FIG. 12 is a set of line graphs showing the results of Example 6, indicating that DNA is taken up into virus-like structures formed from VP1 under prescribed conditions.

Identification of VP2 Portion as Particle Formation Acceleration Factor Contributing to Extracellular Formation of Virus-like Structure of VP1 Protein In order to determine the region of the SV40 capsid protein VP2 acting as a particle formation acceleration factor necessary for formation of virus-like structures from SV40 VP1 protein, 0.44 μM of the different regions of VP2 protein (full-length amino acid sequence as listed in SEQ ID NO: 1) shown in FIG. 10 and 2.2 μM of SV40 VP1 protein were incubated in a solution (pH 5.0) containing 150 mM NaCl and 2 mM $CaCl_2$, and the products were observed under an electron microscope. The results are shown in FIG. 10. In this diagram, "V" indicates that a uniform pentameric virus-like structure had been formed, "Ti" indicates microparticles, "(−)" indicates that no particles were formed, and "Tu" indicates that tube-like structures were formed.

As clearly seen from the results in FIG. 10, in order for SV40 capsid protein VP2 to function as a particle formation acceleration factor, it must include at least the amino acid sequence from residues 1 to 58 and the amino acid sequence from residues 119 to 272 of the amino acid sequence of SEQ ID NO: 1.

Example 5

Determination of Region of VP2 Necessary for Intracellular Incorporation of VP2 into Virus-like Structures It has been reported that co-expressing SV40 VP2 or VP3 protein (VP3 has the same C-terminal sequence as VP2) with VP1 in insect cells results in inclusion of VP2 and VP3 inside the formed VLP. This phenomenon was utilized to examine the possibility of encapsulating a bioactive substance into virus-like structures composed of VP1, by fusing GFP to VP2, VP3 or different fragments thereof and co-expressing the fusion proteins with VP1 to examine whether the fusion proteins were included in the virus-like structures.

Experiment Method

The fusion proteins used were VP2 protein, VP3 protein (partial VP2 protein) and four different C-terminal fragments of VP2 protein (VP3 protein) comprising the VP1-binding region (residues 273 to 307 of VP2) (total of 6 different proteins), each fused with the GFP at the N-terminal or C-terminal end (total of 12 different fusion proteins). The structures of these 12 different fusion proteins are illustrated in FIG. 11. Baculovirus expressing each of these fusion proteins was prepared, and insect cells were coinfected with each fusion protein-expressing baculovirus and VP1-expressing baculovirus.

After 84 hours, the cells were recovered with a scraper and rinsed with ice-cooled PBS(−). The cells were disrupted by ultrasonic disruption. Next, 500 μl of sonication buffer (20 mM Tris-HCl (pH 7.9), 1% sodium deoxycholate (DOC), 2 mM phenylmethylsulfonyl fluoride (PMSF), 1 μg/ml chymostatin, aprotinin, leupeptin, antipain, pepstatin) was added to each 10 cm-diameter dish, and an ultrasonic disruptor was used while cooling on ice until the solution became transparent. After the ultrasonic disruption, the mixture was centrifuged for 10 minutes at 15,000×g, 4° C. and the supernatant was used as the cell lysate. A portion of the cell lysate was separated by SDS-PAGE, Western blotting was performed with anti-VP1 polyclonal antibody and anti-GFP monoclonal antibody (Roche), and expression of VP1 protein and GFP fusion protein was confirmed.

The prepared cell lysate was combined with 20 mM Tris-HCl (pH 7.9) to 20 μl, and layered onto 0.6 ml of 20% to 40% (w/v) sucrose density gradient dissolved in 20 mM Tris-HCL (pH 7.9), already prepared in a 5×41 mm open top tube (Bekman). A specialized adaptor was used to anchor the tube in an SW55Ti rotor for centrifugation at 50,000 rpm, 4° C. for one hour. After centrifugation, 55 μl of each solution was fractionated from the top of the tube, and the 12th fraction was obtained by adding 20 mM Tris-HCl (pH 7.9) to the remaining sample to 55 μl and recovering as a wash from the bottom of the tube. After separating 10 μl of each fraction by SDS-PAGE, Western blotting was performed with anti-VP1 polyclonal antibody and anti-GFP monoclonal antibody (Roche). If VLP is formed in the insect cells, a peak for VP1 protein is detected in the 7th to 10th fractions. Detection of a peak for the GFP fusion protein in the 7th to 10th fractions together with a peak for VLP suggests that it has been included in the formed VLP. Inclusion of the fusion protein in the virus-like structures was examined in this manner.

The results are shown in FIG. 11.

As clearly shown by these results, with fusion of GFP to the C-terminal end of a VP2 protein fragment comprising at least the VP1-binding region, the fusion protein could be taken up by virus-like structures formed from VP1.

This result suggests that if a bioactive substance of interest, instead of GFP, is linked to VP2 or a fragment thereof containing the VP1-binding region, the bioactive substance can be taken up into virus-like structures.

Example 6

In vitro Incorporation of DNA into Virus-like Structures

SV40 VP1 protein and DNA were combined in a weight ratio of VP1:DNA=600:0-1, and after cooling for 30 minutes on ice, the mixture was dialyzed against a solution containing 150 mM NaCl and 2 mM $CaCl_2$ (pH 5) at room temperature for 16 hours. A portion of the dialysate was used for electron microscope observation and for protein quantitation (input protein), while another portion was subjected to centrifugation using a sucrose cushion and the particulate substance and DNA were recovered. The recovered substance was used for measurement of (1) protein (amount of protein forming particles), (2) the amount of DNA after decomposition of protein with Pronase K (amount of input DNA) and (3) the amount of DNA remaining after decomposition removal of non-encapsulated DNA by DNase and decomposition of protein by Pronase K (DNA encapsulated in particles).

The results are shown in FIGS. 12 and 13. As clearly seen from FIG. 12, DNA was incorporated into VP1 virus-like structures when the amount of DNA was at least 0.2 part by weight to 600 parts by weight of VP1 protein.

Example 7

Formation of Virus-like Particles Incorporating RNA

RNA was mixed with purified VP1 pentamer protein. The mixture was solvent-exchanged at room temperature at physiological conditions using a dialysis method. An electron microscope was used for observation of the aggregated state of VP1 pentamers in the exchanged solvent.

For example, 20 µl of 500 ng/µl concentration VP1 pentamer and 0.79 µl of 938.7 ng/µl concentration total RNA were combined and adjusted to a volume of 100 µl a with a 20 mM Tris-HCl (pH 7.9), 150 mM NaCl, 5 mM EGTA, 5 mM DTT solution. The solution was incubated at 4° C., 30 min and exchanged with a pH 5, 150 mM NaCl, 2 mM CaCl$_2$ solution by dialysis for 16 hours at room temperature. The solution was recovered, and an electron microscope was used for observation of the aggregated state of VP1 pentamers in the exchanged solvent. The results are shown in FIG. 14. It is seen that addition of total RNA formed globular virus-like particles.

Industrial Applicability

Particles cannot be formed by allowing high-concentration SV40 VP1 pentamers to stand under physiological conditions. For example, when approximately 80 ng/μL of VP1 pentamer is allowed to stand in a pH 5 to 7 solution containing 150 mM NaCl, 2 mM $CaCl_2$, only tube-like structures or amorphous aggregates are formed. However, addition of VP2 protein at a concentration of approximately 15 to 20 ng/μL under the same conditions can efficiently form uniform-sized particles. Formation of uniform-sized virus-like particles was also observed under high pH conditions of pH 8.0 to 10.0, without VP2 protein. In other words, it has become possible to produce viral particle-like structures under the physiological conditions of low salt concentration and a pH between 5 and 10.

We claim:

1. A method of forming a uniform-sized viral particle-like structure comprising
   (1) a viral protein which is a purified VP1 capsid protein of an SV40 virus, or a mutant thereof which is
      (a) a mutant A (mtA) comprising $^{160}$Glu substitution in SEQ ID NO: 2, by Gln;
      (b) a mutant B (mtB) comprising $^{163}$Glu substitution in SEQ ID NO: 2, by Gln;
      (c) a mutant C (mtC) comprising $^{348}$Asp substitution in SEQ ID NO: 2, by Asn;
      (d) a mutant D (mtD) comprising $^{160}$Glu and $^{163}$Glu substitutions in SEQ ID NO: 2, both by Gln;
      (e) a mutant E (mtE) comprising $^{160}$Glu, $^{163}$Glu and $^{348}$Asp substitutions in SEQ ID NO: 2, wherein Glu is substituted by Gln and Asp is substituted by Asn;
      (f) a mutant F (mtF) comprising $^{332}$Glu, $^{333}$Glu and $^{348}$Asp substitutions in SEQ ID NO: 2, wherein Glu is substituted by Gln and Asp is substituted by Asn;
      (g) a mutant G (mtG) comprising $^{49}$Glu and $^{51}$Glu substitutions in SEQ ID NO: 2, wherein Glu is substituted by Gln; or
      (h) a mutant H (mtH) comprising $^{49}$Glu, $^{51}$Glu, $^{160}$Glu, $^{163}$Glu, $^{216}$Ser, $^{217}$Lys, $^{219}$Glu, $^{332}$Glu, $^{333}$Glu and $^{348}$Asp substitutions in SEQ ID NO: 2, wherein Glu is substituted by Gln, Asp is substituted by Asn, Ser is substituted by Ala and Lys is substituted by Ala;
   (2) a particle formation acceleration factor which is
      a purified fragment of a purified VP2 capsid protein of an SV40 virus comprising amino acids 1 to 272 of the amino acid sequence set forth in SEQ ID NO: 1 or a variant thereof comprising said sequence of SEQ ID NO: 1 with the proviso that (a) Pro, Gly, Gly from positions 283 to 285 in said SEQ ID NO: 1 is mutated to Arg, Glu, Arg (PGP→RER);
(b) Phe at position 276 and Ile at position 277 in said SEQ ID NO: 1 mutated to Glu (FI→EE);
(c) Phe at position 276 and Ile at position 277 in said SEQ ID NO: 1 mutated to Ala (FI→AA); or
(d) Leu at position 296 and Leu at position 300 in said SEQ ID NO: 1 mutated to Ala (LPLLL→APLLA); and (3) a substance to be encapsulated;
said method comprising incubating said viral protein, said particle formation acceleration factor and said substance to be encapsulated at pH 5 to 10 at room temperature, in the presence of 130 mM to 500 mM monovalent cation and 2 mM to 50 mM divalent cation.

2. The method according to claim 1, wherein the monovalent cation is sodium ion.

3. The method according to claim 1, wherein the divalent cation is calcium ion.

4. The method according to claim 1, wherein the concentration of the monovalent cation is 150 mM, and the concentration of the divalent cation is 2 mM.

5. A method of forming uniform-sized viral particle-like structure comprising
(1) a viral protein which is a purified VP1 capsid protein of an SV40 virus;
(2) a viral particle acceleration factor which is a purified SV40 VP2 capsid protein comprising the amino acid sequence set forth in SEQ ID NO: 1; and
(3) a substance to be encapsulated;
said method comprising incubating said purified viral protein, said purified viral particle formation acceleration factor and said substance to be encapsulated at pH 5 to 10 at room temperature, in the presence of 130 mM to 500 mM monovalent cation and 2 mM to 50 mM divalent cation.

6. The method according to claim 1, wherein the substance to be encapsulated is a bioactive substance or a non-bioactive substance, or a mixture thereof.

7. The method according to claim 6, wherein the non-bioactive substance is a low molecular substance, a high molecular substance or a mixture thereof.

8. The method according to claim 6, wherein the bioactive substance is a nucleic acid, a protein or a low molecular-weight substance.

9. A method of introducing a bioactive substance into a uniform-sized viral particle-like structure, comprising coexpressing, in a host cell,
(1) a viral protein which is a VP1 capsid protein of an SV40 virus; and
(2) a particle formation acceleration factor which is
a fragment of a VP2 capsid protein comprising amino acids 1 to 272 of the amino acid sequence set forth in SEQ ID NO: 1, wherein the particle formation acceleration factor further comprises said bioactive substance linked thereto.

10. The method of claim 1, wherein the substance to be encapsulated is a polymer comprising a negatively charged surface, said method comprising mixing, 360 parts by weight of a viral protein which is the VP1 capsid protein of an SV40 virus or the mutant thereof with 0.01 to 100 parts by weight of the polymer, and dialyzing the mixture against an aqueous solution comprising a monovalent metal ion and a divalent metal ion.

11. The method according to claim 10, wherein the negatively charged polymer is a DNA, an RNA or a synthetic nucleic acid.

12. The method according to claim 10, wherein the weight ratio of the negatively charged polymer and the viral protein is at least 0.2.

13. The method according to claim 10, wherein the viral protein is a VP1capsid protein of an SV40 virus.

14. The method according to claim 13, wherein the viral protein is a VP1capsid protein of an SV40 virus comprising the amino acid sequence set forth in SEQ ID NO: 2.

15. The method according to claim 10, wherein the monovalent metal ion is a sodium ion, and the divalent metal ion is a calcium ion.

16. A method of forming uniform-sized viral particle-like structure comprising incubating a mixture consisting essentially of
(1) a viral protein which is a purified VP1 capsid protein of an SV40 virus;
(2) a particle formation acceleration factor which is
(a) a purified VP2 capsid protein of an SV40 virus; or
(b) a purified fragment of a VP2 capsid protein of (2)(a) comprising amino acids 1 to 272 of the amino acid sequence set forth in SEQ ID NO: 1; and
(3) a substance to be encapsulated;
at pH 5 to 10 at room temperature, in the presence of 130 mM to 500 mM monovalent cation and 2 mM to 50 mM divalent cation; and
obtaining said uniform-sized viral particle-like structure thus formed which comprises the encapsulated substance.

17. The method according to claim 16, wherein the mixture consists essentially of a purified VP1 capsid protein of an SV40 virus; a purified VP2 capsid protein of an SV40virus comprising the amino acid sequence set forth in SEQ ID NO: 1; and the substance to be encapsulated.

18. The method according to claim 1, wherein the VP1 capsid protein comprises the amino acid sequence of SEQ ID NO: 2.

19. The method according to claim 1, wherein the particle formation acceleration factor is
(a) a VP2 capsid protein comprising the amino acid sequence of SEQ ID NO: 1; or
(b) a variant of the VP2 capsid protein of (a) which variant comprises said sequence of SEQ ID NO: 1with the proviso that
(a) Pro, Gly, Gly from positions 283 to 285 in said SEQ ID NO: 1 is mutated to Arg, Glu, Arg (PGP→RER);
(b) Phe at position 276 and Ile at position 277 in said SEQ ID NO: 1 mutated to Glu (FI→EE);
(c) Phe at position 276 and Ile at position 277 in said SEQ ID NO: 1 mutated to Ala (FI→AA); or
(d) Leu at position 296 and Leu at position 300 in said SEQ ID NO: 1 mutated to Ala (LPLLL→APLLA).

* * * * *

SEQUENCE LISTING

```
<160> NUMBER OF SEQ ID NOS: 10

<210> SEQ ID NO 1
<211> LENGTH: 352
<212> TYPE: PRT
<213> ORGANISM: Simian virus 40

<400> SEQUENCE: 1

Met Gly Ala Ala Leu Thr Leu Leu Gly Asp Leu Ile Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Leu Ala Ser Val Ala Thr Val
        35                  40                  45

Glu Gly Leu Thr Thr Ser Glu Ala Ile Ala Ala Ile Gly Leu Thr Pro
    50                  55                  60

Gln Ala Tyr Ala Val Ile Ser Gly Ala Pro Ala Ala Ile Ala Gly Phe
65                  70                  75                  80

Ala Ala Leu Leu Gln Thr Val Thr Gly Val Ser Ala Val Ala Gln Val
                85                  90                  95

Gly Tyr Arg Phe Phe Ser Asp Trp Asp His Lys Val Ser Thr Val Gly
            100                 105                 110

Leu Tyr Gln Gln Pro Gly Met Ala Val Asp Leu Tyr Arg Pro Asp Asp
        115                 120                 125

Tyr Tyr Asp Ile Leu Phe Pro Gly Val Gln Thr Phe Val His Ser Val
    130                 135                 140

Gln Tyr Leu Asp Pro Arg His Trp Gly Pro Thr Leu Phe Asn Ala Ile
145                 150                 155                 160

Ser Gln Ala Phe Trp Arg Val Ile Gln Asn Asp Ile Pro Arg Leu Thr
                165                 170                 175

Ser Gln Glu Leu Glu Arg Arg Thr Gln Arg Tyr Leu Arg Asp Ser Leu
            180                 185                 190

Ala Arg Phe Leu Glu Glu Thr Thr Trp Thr Val Ile Asn Ala Pro Val
        195                 200                 205

Asn Trp Tyr Asn Ser Leu Gln Asp Tyr Tyr Ser Thr Leu Ser Pro Ile
    210                 215                 220
```

```
Arg Pro Thr Met Val Arg Gln Val Ala Asn Arg Glu Gly Leu Gln Ile
225                 230                 235                 240

Ser Phe Gly His Thr Tyr Asp Asn Ile Asp Glu Ala Asp Ser Ile Gln
            245                 250                 255

Gln Val Thr Glu Arg Trp Glu Ala Gln Ser Gln Ser Pro Asn Val Gln
        260                 265                 270

Ser Gly Glu Phe Ile Glu Lys Phe Glu Ala Pro Gly Gly Ala Asn Gln
    275                 280                 285

Arg Thr Ala Pro Gln Trp Met Leu Pro Leu Leu Gly Leu Tyr Gly
290                 295                 300

Ser Val Thr Ser Ala Leu Lys Ala Tyr Glu Asp Gly Pro Asn Lys Lys
305                 310                 315                 320

Lys Arg Lys Leu Ser Arg Gly Ser Ser Gln Lys Thr Lys Gly Thr Ser
            325                 330                 335

Ala Ser Ala Lys Ala Arg His Lys Arg Arg Asn Arg Ser Ser Arg Ser
            340                 345                 350
```

<210> SEQ ID NO 2
<211> LENGTH: 364
<212> TYPE: PRT
<213> ORGANISM: Simian virus 40

<400> SEQUENCE: 2

```
Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Asp Lys Glu Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255
```

```
Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
            275                 280                 285

Phe Lys Ile Thr Leu Arg Lys Arg Ser Val Lys Asn Pro Tyr Pro Ile
        290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Pro Leu Leu Leu
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Pro Leu Leu Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Arg Leu Leu Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Leu Leu Ala
1               5
```

```
<210> SEQ ID NO 7
<211> LENGTH: 352
<212> TYPE: PRT
<213> ORGANISM: Simian virus 40

<400> SEQUENCE: 7

Met Gly Ala Ala Leu Thr Leu Leu Gly Asp Leu Ile Ala Thr Val Ser
1               5                   10                  15

Glu Ala Ala Ala Thr Gly Phe Ser Val Ala Glu Ile Ala Ala Gly
            20                  25                  30

Glu Ala Ala Ala Ile Glu Val Gln Leu Ala Ser Val Ala Thr Val
        35                  40                  45

Glu Gly Leu Thr Thr Ser Glu Ala Ile Ala Ala Ile Gly Leu Thr Pro
50                  55                  60

Gln Ala Tyr Ala Val Ile Ser Gly Ala Pro Ala Ala Ile Ala Gly Phe
65                  70                  75                  80

Ala Ala Leu Leu Gln Thr Val Thr Gly Val Ser Ala Val Ala Gln Val
                85                  90                  95

Gly Tyr Arg Phe Phe Ser Asp Trp Asp His Lys Val Ser Thr Val Gly
            100                 105                 110

Leu Tyr Gln Gln Pro Gly Met Ala Val Asp Leu Tyr Arg Pro Asp Asp
        115                 120                 125

Tyr Tyr Asp Ile Leu Phe Pro Gly Val Gln Thr Phe Val His Ser Val
130                 135                 140

Gln Tyr Leu Asp Pro Arg His Trp Gly Pro Thr Leu Phe Asn Ala Ile
145                 150                 155                 160

Ser Gln Ala Phe Trp Arg Val Ile Gln Asn Asp Ile Pro Arg Leu Thr
                165                 170                 175

Ser Gln Glu Leu Glu Arg Arg Thr Gln Arg Tyr Leu Arg Asp Ser Leu
            180                 185                 190

Ala Arg Phe Leu Glu Glu Thr Thr Trp Thr Val Ile Asn Ala Pro Val
        195                 200                 205

Asn Trp Tyr Asn Ser Leu Gln Asp Tyr Tyr Ser Thr Leu Ser Pro Ile
210                 215                 220

Arg Pro Thr Met Val Arg Gln Val Ala Asn Arg Glu Gly Leu Gln Ile
225                 230                 235                 240

Ser Phe Gly His Thr Tyr Asp Asn Ile Asp Glu Ala Asp Ser Ile Gln
                245                 250                 255

Gln Val Thr Glu Arg Trp Glu Ala Gln Ser Gln Ser Pro Asn Val Gln
            260                 265                 270

Ser Gly Glu Ala Ala Glu Lys Phe Glu Ala Pro Gly Ala Asn Gln
        275                 280                 285

Arg Thr Ala Pro Gln Trp Met Leu Pro Leu Leu Leu Gly Leu Tyr Gly
290                 295                 300

Ser Val Thr Ser Ala Leu Lys Ala Tyr Glu Asp Gly Pro Asn Lys Lys
305                 310                 315                 320

Lys Arg Lys Leu Ser Arg Gly Ser Ser Gln Lys Thr Lys Gly Thr Ser
                325                 330                 335

Ala Ser Ala Lys Ala Arg His Lys Arg Arg Asn Arg Ser Ser Arg Ser
            340                 345                 350

<210> SEQ ID NO 8
<211> LENGTH: 352
<212> TYPE: PRT
<213> ORGANISM: Simian virus 40
```

<400> SEQUENCE: 8

```
Met Gly Ala Ala Leu Thr Leu Leu Gly Asp Leu Ile Ala Thr Val Ser
1               5                   10                  15

Glu Ala Ala Ala Thr Gly Phe Ser Val Ala Glu Ile Ala Ala Gly
            20                  25                  30

Glu Ala Ala Ala Ile Glu Val Gln Leu Ala Ser Val Ala Thr Val
            35                  40                  45

Glu Gly Leu Thr Thr Ser Glu Ala Ile Ala Ala Ile Gly Leu Thr Pro
50                      55                  60

Gln Ala Tyr Ala Val Ile Ser Gly Ala Pro Ala Ala Ile Ala Gly Phe
65                  70                  75                  80

Ala Ala Leu Leu Gln Thr Val Thr Gly Val Ser Ala Val Ala Gln Val
                85                  90                  95

Gly Tyr Arg Phe Phe Ser Asp Trp Asp His Lys Val Ser Thr Val Gly
                100                 105                 110

Leu Tyr Gln Gln Pro Gly Met Ala Val Asp Leu Tyr Arg Pro Asp Asp
            115                 120                 125

Tyr Tyr Asp Ile Leu Phe Pro Gly Val Gln Thr Phe Val His Ser Val
130                 135                 140

Gln Tyr Leu Asp Pro Arg His Trp Gly Pro Thr Leu Phe Asn Ala Ile
145                 150                 155                 160

Ser Gln Ala Phe Trp Arg Val Ile Gln Asn Asp Ile Pro Arg Leu Thr
                165                 170                 175

Ser Gln Glu Leu Glu Arg Arg Thr Gln Arg Tyr Leu Arg Asp Ser Leu
            180                 185                 190

Ala Arg Phe Leu Glu Glu Thr Thr Trp Thr Val Ile Asn Ala Pro Val
        195                 200                 205

Asn Trp Tyr Asn Ser Leu Gln Asp Tyr Tyr Ser Thr Leu Ser Pro Ile
210                 215                 220

Arg Pro Thr Met Val Arg Gln Val Ala Asn Arg Glu Gly Leu Gln Ile
225                 230                 235                 240

Ser Phe Gly His Thr Tyr Asp Asn Ile Asp Glu Ala Asp Ser Ile Gln
                245                 250                 255

Gln Val Thr Glu Arg Trp Glu Ala Gln Ser Gln Ser Pro Asn Val Gln
            260                 265                 270

Ser Gly Glu Glu Glu Lys Phe Glu Ala Pro Gly Gly Ala Asn Gln
            275                 280                 285

Arg Thr Ala Pro Gln Trp Met Leu Pro Leu Leu Leu Gly Leu Tyr Gly
        290                 295                 300

Ser Val Thr Ser Ala Leu Lys Ala Tyr Glu Asp Gly Pro Asn Lys Lys
305                 310                 315                 320

Lys Arg Lys Leu Ser Arg Gly Ser Ser Gln Lys Thr Lys Gly Thr Ser
                325                 330                 335

Ala Ser Ala Lys Ala Arg His Lys Arg Arg Asn Arg Ser Ser Arg Ser
                340                 345                 350
```

<210> SEQ ID NO 9
<211> LENGTH: 352
<212> TYPE: PRT
<213> ORGANISM: Simian virus 40

<400> SEQUENCE: 9

```
Met Gly Ala Ala Leu Thr Leu Leu Gly Asp Leu Ile Ala Thr Val Ser
1               5                   10                  15
```

Glu Ala Ala Ala Ala Thr Gly Phe Ser Val Ala Glu Ile Ala Ala Gly
            20                  25                  30

Glu Ala Ala Ala Ala Ile Glu Val Gln Leu Ala Ser Val Ala Thr Val
            35                  40                  45

Glu Gly Leu Thr Thr Ser Glu Ala Ile Ala Ala Ile Gly Leu Thr Pro
        50                  55                  60

Gln Ala Tyr Ala Val Ile Ser Gly Ala Pro Ala Ala Ile Ala Gly Phe
65                  70                  75                  80

Ala Ala Leu Leu Gln Thr Val Thr Gly Val Ser Ala Val Ala Gln Val
                85                  90                  95

Gly Tyr Arg Phe Phe Ser Asp Trp Asp His Lys Val Ser Thr Val Gly
                100                 105                 110

Leu Tyr Gln Gln Pro Gly Met Ala Val Asp Leu Tyr Arg Pro Asp Asp
            115                 120                 125

Tyr Tyr Asp Ile Leu Phe Pro Gly Val Gln Thr Phe Val His Ser Val
            130                 135                 140

Gln Tyr Leu Asp Pro Arg His Trp Gly Pro Thr Leu Phe Asn Ala Ile
145                 150                 155                 160

Ser Gln Ala Phe Trp Arg Val Ile Gln Asn Asp Ile Pro Arg Leu Thr
                165                 170                 175

Ser Gln Glu Leu Glu Arg Arg Thr Gln Arg Tyr Leu Arg Asp Ser Leu
            180                 185                 190

Ala Arg Phe Leu Glu Glu Thr Thr Trp Thr Val Ile Asn Ala Pro Val
            195                 200                 205

Asn Trp Tyr Asn Ser Leu Gln Asp Tyr Tyr Ser Thr Leu Ser Pro Ile
210                 215                 220

Arg Pro Thr Met Val Arg Gln Val Ala Asn Arg Glu Gly Leu Gln Ile
225                 230                 235                 240

Ser Phe Gly His Thr Tyr Asp Asn Ile Asp Glu Ala Asp Ser Ile Gln
                245                 250                 255

Gln Val Thr Glu Arg Trp Glu Ala Gln Ser Ser Pro Asn Val Gln
            260                 265                 270

Ser Gly Glu Phe Ile Glu Lys Phe Glu Ala Arg Glu Arg Ala Asn Gln
        275                 280                 285

Arg Thr Ala Pro Gln Trp Met Leu Pro Leu Leu Gly Leu Tyr Gly
        290                 295                 300

Ser Val Thr Ser Ala Leu Lys Ala Tyr Glu Asp Gly Pro Asn Lys Lys
305                 310                 315                 320

Lys Arg Lys Leu Ser Arg Gly Ser Ser Gln Lys Thr Lys Gly Thr Ser
                325                 330                 335

Ala Ser Ala Lys Ala Arg His Lys Arg Arg Asn Arg Ser Ser Arg Ser
                340                 345                 350

<210> SEQ ID NO 10
<211> LENGTH: 352
<212> TYPE: PRT
<213> ORGANISM: Simian virus 40

<400> SEQUENCE: 10

Met Gly Ala Ala Leu Thr Leu Leu Gly Asp Leu Ile Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Leu Ala Ser Val Ala Thr Val
            35                  40                  45

```
Glu Gly Leu Thr Thr Ser Glu Ala Ile Ala Ala Ile Gly Leu Thr Pro
 50                  55                  60
Gln Ala Tyr Ala Val Ile Ser Gly Ala Pro Ala Ala Ile Ala Gly Phe
 65                  70                  75                  80
Ala Ala Leu Leu Gln Thr Val Thr Gly Val Ser Ala Val Ala Gln Val
                 85                  90                  95
Gly Tyr Arg Phe Phe Ser Asp Trp Asp His Lys Val Ser Thr Val Gly
            100                 105                 110
Leu Tyr Gln Gln Pro Gly Met Ala Val Asp Leu Tyr Arg Pro Asp Asp
        115                 120                 125
Tyr Tyr Asp Ile Leu Phe Pro Gly Val Gln Thr Phe Val His Ser Val
        130                 135                 140
Gln Tyr Leu Asp Pro Arg His Trp Gly Pro Thr Leu Phe Asn Ala Ile
145                 150                 155                 160
Ser Gln Ala Phe Trp Arg Val Ile Gln Asn Asp Ile Pro Arg Leu Thr
                165                 170                 175
Ser Gln Glu Leu Glu Arg Arg Thr Gln Arg Tyr Leu Arg Asp Ser Leu
            180                 185                 190
Ala Arg Phe Leu Glu Glu Thr Thr Trp Thr Val Ile Asn Ala Pro Val
        195                 200                 205
Asn Trp Tyr Asn Ser Leu Gln Asp Tyr Tyr Ser Thr Leu Ser Pro Ile
        210                 215                 220
Arg Pro Thr Met Val Arg Gln Val Ala Asn Arg Glu Gly Leu Gln Ile
225                 230                 235                 240
Ser Phe Gly His Thr Tyr Asp Asn Ile Asp Glu Ala Asp Ser Ile Gln
                245                 250                 255
Gln Val Thr Glu Arg Trp Glu Ala Gln Ser Gln Ser Pro Asn Val Gln
            260                 265                 270
Ser Gly Glu Phe Ile Glu Lys Phe Glu Ala Pro Gly Gly Ala Asn Gln
        275                 280                 285
Arg Thr Ala Pro Gln Trp Met Ala Pro Leu Leu Ala Gly Leu Tyr Gly
        290                 295                 300
Ser Val Thr Ser Ala Leu Lys Ala Tyr Glu Asp Gly Pro Asn Lys Lys
305                 310                 315                 320
Lys Arg Lys Leu Ser Arg Gly Ser Ser Gln Lys Thr Lys Gly Thr Ser
                325                 330                 335
Ala Ser Ala Lys Ala Arg His Lys Arg Arg Asn Arg Ser Ser Arg Ser
            340                 345                 350
```